United States Patent

Kathawala

[11] 4,320,135
[45] Mar. 16, 1982

[54] INHIBITING GROWTH HORMONE SECRETION WITH 5,5-SUBSTITUTED HYDANTOIN DERIVATIVES

[75] Inventor: Faizulla G. Kathawala, Mountain Lakes, N.J.

[73] Assignee: Sandoz, Inc., East Hanover, N.J.

[21] Appl. No.: 151,333

[22] Filed: May 19, 1980

[51] Int. Cl.³ ............... A61K 31/415; C07D 491/107
[52] U.S. Cl. .................. 424/273 R; 260/333; 260/345.9 R; 260/347.8; 548/309
[58] Field of Search .................. 548/309; 424/273 R

[56] References Cited

FOREIGN PATENT DOCUMENTS 1315630 5/1973 United Kingdom .
1321799 6/1973 United Kingdom .

OTHER PUBLICATIONS

*Chemical Abstracts,* 83:28051e (1975) [Tosunyan, A. et al., *Arm. Khim. Zh.,* 1975, 28(1), 42–47].
*Chemical Abstracts,* 78:4239t (1973) [Ger. Ols. 2,215,721, Fosker et al., Oct. 5, 1972].

*Primary Examiner*—Richard A. Schwartz
*Attorney, Agent, or Firm*—Gerald D. Sharkin; Richard E. Vila; Frederick H. Weinfeldt

[57] ABSTRACT

The compounds are free hydantoin derivatives of the formula:

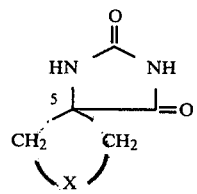

wherein X is a divalent radical consisting of from 2 to 5 linked units; one unit being —O—, and from one to 4 hydrocarbon units, independently, having the structure (a) —CH$_2$— or (b) —C(R)$_2$— in which R is alkyl having from 1 to 6 carbon atoms and being free of branching on the α-carbon atoms; provided that no more than 2 units are of type b; or a pharmaceutically acceptable salt form thereof with a suitable cation; e.g. 7-oxa-1,3-diazaspiro[4.4]nonane-2,4-dione, and are useful as pharmaceuticals.

11 Claims, No Drawings

INHIBITING GROWTH HORMONE SECRETION WITH 5,5-SUBSTITUTED HYDANTOIN DERIVATIVES

This invention relates to organic compounds and more particularly to 5,5-substituted hydantoin derivatives, and to their use as pharmaceutical agents, as well as to pharmaceutical compositions containing such compounds.

The compounds involved in this invention are conveniently represented by the formula I:

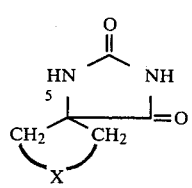
                                                    I wherein X is a divalent radical consisting of from 2 to 5 linked units; one unit being —O—, and from one to 4 hydrocarbon units, independently, having the structure —$CH_2$— or —$C(R)_2$— in which R is alkyl having from 1 to 6 carbon atoms and being free of branching on the α-carbon atoms; provided that no more than 2 units are of the —$C(R)_2$— type.

It will be appreciated that the radical X serves as a bridge and completes a oxa-cycloalkyl ring, which shares the 5-carbon atom of the hydantoin nucleus. Since 4 ring members are contributed by the shared carbon atom, two methylene units (each attached thereto) and the one oxygen unit in X, the total number of ring members in the oxa-cycloalkyl ring is 4+the number of hydrocarbon units contributed by X. As the minimum number of hydrocarbon units contributed by X is one, and the maximum is 4, the minimum ring size is 5 and the maximum is 8. When the number of hydrocarbon units of the $C(R)_2$— type is at the maximum, ie two, then up to two of the hydrocarbon units can be methylene units.

Compounds I may be viewed as consisting of 3 sub-classes, depending on whether 0, 1 or 2 —$C(R)_2$— units are present:

(1) Compounds Ia, ie Compounds I in which none of the units is —$C(R)_2$—:

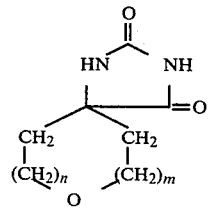
                                                    Ia in which
n is a whole number of from 0 to 2; and
m is a whole number of from 1 to 4; provided that the total ring carbon atoms in n and m is from 1 to 4;

(2) Compounds Ib:

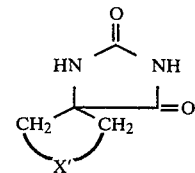
                                                    Ib in which X′ is the same as X as defined above, except that one unit is of the —$C(R)_2$— type (R being as defined above); and (3) Compounds Ic:

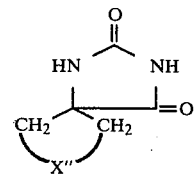
                                                    Ic in which X″ is the same as X as defined above, except that two units are of the —$C(R)_2$— type (R being as defined above).

Compounds I are obtainable by adaptation of methods described in the literature for the preparation of 5,5-substituted hydantoins. A convenient method of obtaining Compounds I comprises reacting an oxa-cycloalkyl ketone of the formula II

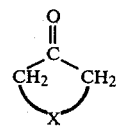
                                                    II in which X is as defined above, with potassium or sodium cyanide, preferably KCN, and ammonium carbonate in an aqueous medium (process a). Suitable reaction temperatures are from about 40° to 80° C., preferably from about 50° to 65°, eg about 55° C. It is preferable to include a water-miscible co-solvent, eg a lower alkanol, such as ethanol. It is also preferred to use a large excess of ammonium carbonate, eg in 4 to 10 fold excess.

The above-described process (a) for preparing Compounds I may be conveniently represented by Reaction Scheme A, below, in which X is as defined above.

REACTION SCHEME A process (a)

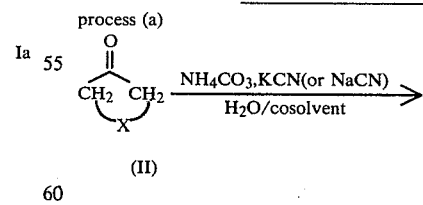

(II)

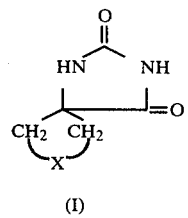

(I)

Many reagents and compounds II employed in the above described reaction are known, a number of which are commercially available. Those that are not known may be prepared by adaptation of methods described in the literature for the preparation of the known compounds.

The products of the processes described herein may be recovered and refined, where such is desired, by conventional means, such as by crystallization, distillation or chromatographic techniques such as column or thin layer chromatography.

Preferred Compounds I are those having one or more of the following attributes; X has 2 or 3 units, eg 2; the hydrocarbon unit(s) of X are of the methylene type; or where any are of the $C(R)_2$-type then R is methyl. A preferred compound I of this invention is 7-oxa-1,3-diazaspiro[4.4]nonane-2,4-dione.

Utility Statement

The compounds I of this invention are useful as pharmaceutical agents in animals. In particular, the compounds of formula I are useful as growth hormone secretion inhibitors. Such activity of the Compounds I is indicated by an assay for inhibition of morphine-induced growth hormone release in male Sprague-Dawley rats (approximately 200 g) after acute or chronic compound pretreatment. Fifteen minutes after morphine/8 mg/kg s.c. or i.p.) administration, the rats are sacrificed by $CO_2$ asphyxiation ("dry ice" in a battery jar). Three cc blood samples are collected, by cardiac puncture, using syringes containing disodium ethylenediaminetetraacetate at 2.5 mg/cc of blood. The samples are centrifuged (2500 RPM, 15 minutes, 4° C.); the serum decanted and stored frozen until radioimmunoassayed for growth hormone levels. The radioimmunoassay may be carried out by standard means against samples from a control group.

Inhibitors of growth hormone secretion are useful, inter alia, in preventing or arresting complications of diabetes associated with microangiopathy such as retinopathy or nephropathy, and in treating acromegaly.

When the compounds are employed for the above usage, they may be combined with one or more pharmaceutically acceptable carriers, e.g., solvents, diluents and the like, and may be administered orally in such forms as tablets, capsules, dispersible powders, granules, suspensions containing, for example, from about 0.5 to 5% of suspending agent, syrups containing, for example, from about 10 to 50% of sugar, and elixirs containing, for example, from about 20 to 50% ethanol, and the like, or parenterally in the form of sterile injectable solutions or suspensions eg containing from about 0.5 to 5% suspending agent in an isotonic medium. These pharmaceutical preparations may contain, for example, from about 0.5% up to about 90% of the active ingredient in combination with the carrier, more usually between 5% and 60% by weight.

The particular dosage of a compound I employed (as active ingredient) in inhibiting the activity of growth hormone in a mammal may vary depending on the particular compound employed, the mode of administration and the severity of the condition being treated. However, in general, satisfactory results are obtained when the compounds of formula I are administered at a daily dosage of from about 1 milligram to about 200 milligrams per kilogram of animal body weight, preferably given in divided doses two to four times a day, or in sustained release form. For most large mammals, the total daily dosage is from about 50 milligrams to about 2,000 milligrams, eg from about 100 milligrams to about 1,000 milligrams. Dosage forms suitable for internal use comprise from about 13 to 1,000 milligrams of the active compound in intimate admixture with a solid or liquid pharmaceutically acceptable carrier. Solid carriers include starch, lactose and kaolin, while liquid carriers include sterile water, polyethylene glycols and edible oils such as corn, peanut and sesame oils, as are appropriate to the nature of the active ingredient and the particular form of administration desired. Adjuvants customarily employed in the preparation of pharmaceutical compositions may be advantageously included, such as flavoring agents, coloring agents, preserving agents, and antioxidants eg vitamin E, ascorbic acid, BHT and BHA.

The preferred pharmaceutical compositions from the stand-point of ease of preparation and administration are solid compositions, particularly tablets and hard-filled or liquid-filled capsules. Oral administration is preferred.

For the above-described usage, the compounds of the formula I may be employed in the free form or in pharmaceutically acceptable salt form, e.g. as mono- salts, with suitable cations, such as sodium or potassium. Such salts may be prepared by conventional techniques, for example reacting a Compound I with a corresponding equivalent amount of a base of the desired cation, in a suitable medium, eg a lower alkoxide in the corresponding alcohol, such as a methoxide in methanol; or a hydroxide in water, at moderate temperatures eg 20° to 80° C., and then evaporating off the medium, and further refining as needed.

The following examples illustrate the practice of the invention. All temperatures are centigrade (uncorrected) and room temperature is 20° to 30° C., unless indicated otherwise.

EXAMPLE 1

7-Oxa-1,3-diazaspiro[4.4]nonane-2,4-dione

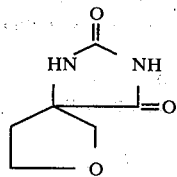

A solution of 19.2 g of ammonium carbonate in 42 ml of ethanol and 28 ml of water is added to 10.0 g of 3-ketotetrahydrofuran. The resulting mixture is heated to 55° and to it is then added, dropwise, a solution of 6.3 g of potassium cyanide in 15 ml of water. The reaction mixture is stirred at 55° for 18 hrs. Thereafter the reaction mixture is evaporated in vacuo to dryness to obtain a residue. The residue is dissolved in a minimum of water and the mixture made acidic with 2 N hydrochloric acid. The first crop of the title product precipitates out on cooling and is filtered off. A second crop of the title product is obtained by concentrating the filtrate and cooling. The two combined crops are recrystalized from ethanol to give refined title product, m.p. 202°–204°.

EXAMPLE 2

Repeating the procedure of Example 1, but in place of the 3-ketotetrahydrofuran used therein, an approximately equivalent amount of:
(a) 3-ketotetrahydropyran;
(b) 3-keto-5,5 dimethyltetrahydrofuran;
(c) 4-keto-2,2-dimethyltetrahydropyran;
(d) 3-keto-2,2-(di-n-butyl)-tetrahydrofuran;
(e) 3-oxacycloheptanone;
(f) 4-ketotetrahydropyran; or
(g) 4-keto-2,2,6,6-tetramethyl tetrahydropyran;
there is accordingly obtained:
(a) 7-oxa-1,3-diazaspiro-[4.5]decane-2,4-dione;
(b) 8,8,-dimethyl-7-oxa-1,3-diazaspiro[4.4]nonane-2,4-dione;
(c) 7,7-dimethyl-8-oxa-1,3-diazaspiro[4.5]decane-2,4-dione;
(d) 8,8-dibutyl-7-oxa-1,3-diazaspiro[4.4]nonane-2,4-dione;
(e) 7-oxa-1,3-diazaspiro[4.6]undecane-2,4-dione;
(f) 8-oxa-1,3-diazaspiro[4.5]decane-2,4-dione; and
(g) 8-oxa-7,7,9,9-tetramethyl-1,3-diazaspiro[4.5]decane-2,4-dione, m.p. 255°–258°.

EXAMPLE 3

Tablets and Capsules

Tablets and capsules containing the ingredients indicated below may be prepared by conventional techniques and are indicated for use at a dose of one tablet or capsule, 2 to 4 times a day, eg at mealtime (3 times/day):

| Ingredient | Weight (mg) tablet | capsule |
|---|---|---|
| 7-oxa-1,3-diazaspiro-[4.4]nonane-2,4-dione | 100 | 100 |
| tragacanth | 10 | — |
| lactose | 247.5 | 300 |
| corn starch | 25 | — |
| talcum | 15 | — |
| magnesium stearate | 2.5 | — |
| Total | 400.0 | 400 |

EXAMPLE 4

Sterile Injectable and Oral Suspensions

The following pharmaceutical compositions are formulated with the indicated amount of active ingredient using conventional techniques. The injectable suspension and the oral liquid suspension represent formulations indicated for use as unit doses. The injectable suspension is indicated for administration once or twice a day, whereas the oral liquid suspension is indicated for administration 2 to 4 times per day, eg at mealtime (3 times per day):

| Ingredients | Weight (mg) sterile injectable suspension | oral liquid suspension |
|---|---|---|
| 7-oxa-1,3-diazaspiro-[4.4] nonane-2,4-dione | 200 | 100 |
| sodium carboxymethyl cellulose U.S.P. | 1.25 | 12.5 |
| methyl cellulose | 0.4 | — |
| polyvinylpyrrolidone | 5 | — |
| lecithin | 3 | — |
| benzyl alcohol | 0.01 | — |
| magnesium aluminum silicate | — | 47.5 |
| flavour | — | q.s. |
| colour | — | q.s. |
| methyl paraben, U.S.P. | — | 4.5 |
| propyl paraben, U.S.P. | — | 1.0 |
| polysorbate 80 (e.g., Tween 80), U.S.P. | — | 5 |
| sorbitol solution, 70%, U.S.P. | — | 2,500 |
| buffer agent to adjust pH for stability | q.s. | q.s. |
| water | for injection q.s. to 1 ml | q.s. to 5 ml |

What is claimed is:

1. A pharmaceutical composition in tablet or capsule unit dose form, suitable for inhibiting growth hormone secretion in a mammal comprising in tablet or capsule unit dose form a non-toxic pharmaceutically-acceptable carrier; and a growth-hormone secretion inhibiting-effective amount of a compound which is (A) a free base of the formula:

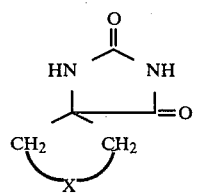

wherein X is a divalent radical consisting of from 2 to 5 linked units; one unit being —O—, and from one to 4 units, independently, having the structure —CH$_2$— (a); or —C(R)$_2$— (b)

in which R is alkyl having from 1 to 6 carbon atoms and being free of branching on the α-carbon atoms; or (B) a pharmaceutically acceptable salt form thereof with a suitable cation.

2. A composition of claim 1 which is in tablet form.
3. A composition of claim 1 which is in capsule form.
4. A composition of claim 1 in which the compound is present in an amount of from about 13 to about 1000 milligrams.
5. A composition of claim 1 in which the compound is 7 oxa-1,3-diazaspiro-[4.4]nonane-2,4-dione.
6. A method of inhibiting growth hormone secretion in a mammal in need of such treatment, comprising administering to said mammal a growth hormone secretion-inhibiting amount of a compound which is (A) a free base of the formula:

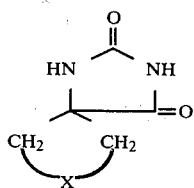

wherein X is a divalent radical consisting of from 2 to 5 linked units; one unit being —O—, and from one to 4 units, independently, having the structure —CH₂— (a); or —C(R)₂— (b)

in which R is alkyl having from 1 to 6 carbon atoms and being free of branching on the α-carbon atoms; or (B) a pharmaceutically acceptable salt form thereof with a suitable cation.

7. A method of claim 6 in which the daily dosage is from about 50 milligrams to about 2000 milligrams.

8. A method of claim 6 in which the daily dosage is from about 100 milligrams to 1000 milligrams.

9. A method of claim 6 in which the compound is 7-oxa-1,3-diazaspiro-[4.4]nonane-2,4-dione.

10. A method of claim 6 in which the treatment is for the purpose of preventing or arresting complications of diabetes associated with microangiopathy.

11. A method of claim 6 in which the condition being treated is acromegaly.

* * * * *